US008940306B2

(12) United States Patent
Matsuda et al.

(10) Patent No.: US 8,940,306 B2
(45) Date of Patent: *Jan. 27, 2015

(54) METHOD FOR ENHANCING IMMUNE RESPONSE WITH PEPTIDE

(71) Applicant: The Chemo-Sero-Therapeutic Research Institute, Kumamoto-shi (JP)

(72) Inventors: Junichi Matsuda, Kikuchi (JP); Kazuyoshi Kaminaka, Kikuchi (JP); Chikateru Nozaki, Kikuchi (JP)

(73) Assignee: The Chemo-Sero-Therapeutic Research Institute, Kumamoto-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/018,495

(22) Filed: Sep. 5, 2013

(65) Prior Publication Data
US 2014/0044743 A1 Feb. 13, 2014

Related U.S. Application Data

(60) Division of application No. 13/220,452, filed on Aug. 29, 2011, now Pat. No. 8,623,374, which is a continuation of application No. 12/596,741, filed as application No. PCT/JP2008/057612 on Apr. 18, 2008, now Pat. No. 8,106,015.

(30) Foreign Application Priority Data

Apr. 20, 2007 (JP) .................................. 2007-112060
Oct. 26, 2007 (JP) .................................. 2007-279083

(51) Int. Cl.
| A61K 38/17 | (2006.01) |
|---|---|
| A61K 39/00 | (2006.01) |
| A61P 25/00 | (2006.01) |
| A61P 37/04 | (2006.01) |
| A61K 31/711 | (2006.01) |
| C07K 14/47 | (2006.01) |
| C07K 14/435 | (2006.01) |

(52) U.S. Cl.
CPC ............ *A61K 39/0007* (2013.01); *A61K 31/711* (2013.01); *C07K 14/4711* (2013.01)
USPC ...... 424/185.1; 514/17.7; 514/17.8; 514/21.3; 530/324

(58) Field of Classification Search
None
See application file for complete search history.

(56) References Cited

U.S. PATENT DOCUMENTS

| 5,589,154 | A | 12/1996 | Anderson |
| 6,787,523 | B1 | 9/2004 | Schenk |
| 8,106,015 | B2 | 1/2012 | Matsuda et al. |
| 8,512,709 | B2 | 8/2013 | Matsuda et al. |
| 2012/0244184 | A1 | 9/2012 | Kaminaka et al. |

FOREIGN PATENT DOCUMENTS

| DE | 199 16 417 A1 | 10/2000 |
| JP | 2004-500354 T | 1/2004 |
| JP | 2004-538332 | 12/2004 |
| JP | 2005-506311 | 3/2005 |
| WO | WO 01/39796 A2 | 6/2001 |
| WO | WO 02/096350 A2 | 12/2002 |
| WO | WO 03/015812 A2 | 2/2003 |
| WO | WO 03/040183 A2 | 5/2003 |
| WO | WO 03/040183 A3 | 5/2003 |
| WO | WO 2005/072777 A2 | 8/2005 |

OTHER PUBLICATIONS

William V. Nikolic, et al., "Transcutaneous β-amyloid immunization reduces cerebral β-amyloid deposits without Tcell infiltration and microhemorrhage", PNAS, vol. 104, No. 7, Feb. 13, 2007, pp. 2507-2512.

Peter J. Wettstein, et al., "Cysteine-Tailed Class I-Binding Peptides Bind to CpG Adjuvant and Enhance Primary CTL Responses", The Journal of Immunology, vol. 175, 2005, pp. 3681-3689.

Elizabeth Head, et al, "Immunization with fibrillar $A\beta_{1-42}$ in young and aged canines: Antibody generation and characteristics, and effects on CSF and brain Aβ", Vaccine, vol. 24, 2006, pp. 2824-2834.

Dan Frenkel, et al., "Immunization against Alzheimer's β-amyloid plaques via EFRH phage administration", PNAS, vol. 97, No. 21, Oct. 10, 2000, pp. 11455-11459.

Dave Morgan, et al, "Aβ peptide vaccination prevents memory loss in an animal model of Alzheimer's disease". Nature, vol. 408, Dec. 21/28, 2000, pp. 982-985.

Dale Schenk, at al., "Immunization with amyloid-β attenuates Alzheimer-disease-like pathology in the PDAPP mouse", Nature, vol. 400, Jul. 8, 1999, pp. 173-177.

N. C. Fox, et al., "Effects of Aβ immunization (AN1792) on MRI measures of cerebral volume in Alzheimer disease", Neurology, vol. 64, 2005, pp. 1563-1572.

James A. R. Nicoll, et al., "Neuropathology of human Alzheimer disease after immunization with amyloid-β peptide: a case report", Nature Medicine, vol. 9, No. 4, Apr. 2003, pp. 448-452.

(Continued)

*Primary Examiner* — Gregory S Emch
*Assistant Examiner* — Adam M Weidner
(74) *Attorney, Agent, or Firm* — Oblon, Spivak, McClelland, Maier & Neustadt, L.L.P.

(57) ABSTRACT

An object of the present invention is to provide a safe and effective method for enhancing an immune response and a medicament for preventing or treating Alzheimer disease comprising amyloid β peptide that induces an enhanced immune response. An amyloid β peptide or a portion thereof with addition or insertion of cysteine and a method for enhancing an immune response using the peptide or a method for enhancing an immune response using the peptide together with an adjuvant. A medicament for preventing or treating Alzheimer disease comprising an amyloid β peptide or a portion thereof that induces an enhanced immune response. A DNA vaccine, that may have the same effect, comprising the gene encoding an amyloid β peptide or a portion thereof that induces an enhanced immune response with addition or insertion of cysteine.

19 Claims, No Drawings

(56) References Cited

OTHER PUBLICATIONS

Hiroshi Takahashi, et al., "Monoclonal antibody to β peptide, recognizing amyloid deposits, neuronal cells and lipofuscin pigments in systemic organs", Acta Neuropathol, vol. 85, No. 2, 1993, pp. 159-166.

Christine M. Rzepczyk, et al., "Synthetic Peptide Immunogens Eliciting Antibodies to *Plasmodium falciparum* Sporozoite and Merozoite Surface Antigens in $H-2^b$ and $H-2^k$ Mice[1]" The Journal of Immunology, vol. 145, No. 8, Oct. 15, 1990, pp. 2691-2696.

Abdul Tawab, et al., "Recombinant IemA without adjuvant induces extensive expansion of H2-M3-restricted CD8 effectors, which can suppress primary listeriosis in mice", International Immunology, vol. 14, No. 2, Nov. 5, 2001, pp. 225-232.

Shiou-Chih Hsu, et al., "Reduction of Respiratory Syncytial Virus Titer in the Lungs of Mice after Intranasal Immunization with a Chimeric Peptide Consisting of a Single CTL Epitope Linked to a Fusion Peptide", Virology, vol. 240, article No. VY978923, 1998, pp. 376-381.

José A. Boga, et al., "A single dose immunization with rabbit haemorrhagic disease virus major capsid protein produced in *Saccharomyces cerevisiae* induces protection", Journal of General Virology, vol. 78, 1997, pp. 2315-2318.

Nacilla Haicheur, et al., "The B subunit of Shiga toxin coupled to full-size antigenic protein elicits humoral and cell-mediated immune responses associated with a $T_n$ 1-dominant polarization", International Immunology, vol. 15, No. 10, Jul. 11, 2003. pp. 1161-1171.

Marilena Manea, et al., Polypeptide Conjugates Comprising a β-Amyloid Plaque-Specific Epitope as New Vaccine Structures Against Alzheimer's Disease, Biopolymers, vol. 76, No. 6, XP009043837, Jan. 1, 2004, pp. 503-511.

Chuanhai Cao, et al., Successful adjuvant-free vaccination of BALB/c mice with mutated amyloid β peptides, MBC Neuroscience, vol. 9, No. 1, XP021033558, Feb. 18, 2008, pp. 1of 11.

Jun-Ichi Matsuda, et al., Amyloid β peptides with an additional cysteine residue can enhance immunogenicity and reduce the amyloid β burden in an Alzheimer's disease mouse model, Biochemical and Biophysical Research Communications, XP026060890, vol. 382, No. 1, Apr. 24, 2009, pp. 149-152.

Vickers 2002 Drugs Aging 19(7): 487-494.

Lee et al., 2006 "Cytosolic amyloid-β peptide 42 escaping from degradation induces cell death" Blochem and Biophys Research Communications 344.

Tsien, 1998, "The Green Fluorescent Protein" Annu Rev Biochem 67.

METHOD FOR ENHANCING IMMUNE RESPONSE WITH PEPTIDE

This application is a divisional of U.S. application Ser. No. 13/220,452 filed on Aug. 29, 2011, which is a Continuation of Ser. No. 12/596,741 filed Oct. 20, 2009, which is a National Stage of PCT/JP08/057612 filed Apr. 18, 2008, the entire content of which is incorporated herein by reference.

TECHNICAL FIELD

The present invention relates to an immunogenic peptide that induces an enhanced immune response, comprising a peptide derived from amyloid β (Aβ), a causative substance of Alzheimer disease, or a portion thereof with addition or insertion of cysteine. The present invention also relates to a medicament for preventing or treating Alzheimer disease which comprises as an active ingredient said peptide. The immunogenic peptide of the present invention, as sufficiently inducing an enhanced immune response by itself without adjuvant, may safely be used as a medicament for the prevention or treatment without an adverse drug reaction associated with the use of adjuvant.

BACKGROUND ART

Immunity is one of self-protecting biological defense mechanisms against invading foreign organisms such as bacteria and viruses and includes innate immunity associated with phagocytosis of leukocytes etc. and acquired immunity against a specific antigen/pathogen. A vaccine is a medicament for safely inducing the acquired immunity against a pathogen and recently has been used not only for protection but also for treatment.

A vaccine includes a live vaccine, an inactivated vaccine, a component vaccine, and the like. A live vaccine is highly immunogenic and has a prolonged immunological effect but also has a risk that pathogenicity remains or is reverted. An inactivated vaccine, prepared by treating viruses with formalin etc. to remove the pathogenicity, is safer than a live vaccine but has a defect that the resulting immunity is not prolonged.

A component vaccine comprises as a main component an antigenic protein, prepared by extracting and purifying a protein having a vaccinal effect from a pathogen or artificially prepared by genetic engineering techniques or chemical procedures, and is highly safe free from contamination of unwanted proteins. Recently, a peptide vaccine as one of component vaccines has been studied profoundly. A peptide refers to a molecule that consists of amino acids bound to each other through peptide linkage. Generally, a peptide with 10 or less amino acid residues is called an oligopeptide, a peptide with less than 100 amino acid residues is called a polypeptide (both an oligopeptide and a polypeptide are herein referred to as a "peptide"), and one with 100 or more amino acid residues is called a protein.

Recently, amino acid sequences of various proteins and viral antigenic proteins have been determined. A peptide artificially synthesized based on such an amino acid sequence is used as a vaccine, which is referred to as a peptide vaccine. The advantage of using a peptide as a vaccine is that a highly pure antigen can be obtained artificially without handling pathogenic microorganisms. On the other hand, it is difficult to obtain a sufficient immune effect since a peptide has a small molecular weight and hence is not recognized as a foreign substance in the living body on immunization. Hence, a peptide is combined with a large protein called a carrier protein so as to be recognized as a foreign substance and/or is administered together with an adjuvant (immunomodulator) in order to enhance immune effect. However, with these treatments, it is possible that an antibody against a carrier protein may be produced or an adverse side effect of an adjuvant may unexpectedly be induced. Besides, while an adjuvant is proved to be effective on research level, it is only an aluminum hydroxide gel that is permitted in Japan for usage in human.

On the other hand, a peptide vaccine has been attempted for use for preventing and/or treating diseases such as Alzheimer disease. Alzheimer disease is one of dementia disorders and is associated with declined cognitive function and change in personality as principal symptoms. The increasing number of patients along with rapid increase of aging population has become a social issue. Alzheimer disease's pathological indications include three features of atrophy and/or fall-off of neurons, formation of senile plaques due to aggregation and/or deposition of Aβ and neurofibrillary changes due to abnormal tau proteins. Onset of Alzheimer disease is initiated by deposition of Aβ peptides (senile plaque formation) followed by denaturing and fall-of of neurons with increase in Aβ deposition. The deposition of Aβ peptides then trigger deposition of tau proteins followed by neurofibrillary changes. Aβ peptide is derived from an amyloid peptide precursor (APP) existing in the brain and the body. In normal process, APP is cleaved by α-secretase in the middle and then by γ-secretase in the C-terminal to generate a P3 peptide which is subsequently degraded completely. In the case of Aβ peptide deposition, APP is cleaved by β-secretase and then by γ-secretase in the C-terminal to generate Aβ peptides consisting of 40 or 42 amino acid resides (Aβ40, Aβ42). Among these, Aβ42, easily aggregated and deposited, is extracellularly secreted to be insolubilized, and aggregated and deposited to form senile plaques. Increase in production and accumulation of Aβ42 peptides would affect a synapse. Further, microglial cells and astrocytes are gathered around the aggregated Aβ peptides. It is thought that damages in the synapse and the neurite further progress to lead to degeneration and cell death of neurons, resulting in dementia.

Nowadays, targeting Aβ peptides, a method of treatment is considered for decreasing Aβ peptides, including, for instance, inhibition of the action of secretases which produce Aβ peptides, use of an Aβ degrading enzyme which may degrade the produced Aβ peptides, use of a vaccine or an antibody for removing those extracellularly excreted and those aggregated, and the like.

Approach of treating Alzheimer disease with a vaccine was first reported by Schenk et al. (Non-patent reference 1), which comprises administering Aβ42 peptides together with an adjuvant by intramuscular injection to thereby produce an antibody against Aβ to remove the accumulated Aβ peptides. A clinical trial for the vaccine was performed by administering intramuscularly a medicament comprising the Aβ42 peptide together with a purified saponin as an adjuvant. As a result, it was shown that an antibody specific to Aβ peptide was produced in Alzheimer disease patients by administration of the vaccine and that the production of the antibody specific to Aβ peptide could retard the development of cognitive disturbance in Alzheimer disease patients (Non-patent reference 2) and it was proved that senile plaques were disappeared (Non-patent reference 3). However, since serious meningoencephalitis was observed in some subjects, the clinical trial was discontinued. It is supposed that one of causes of the adverse side effect is the adjuvant contained in the vaccine. Accordingly, for a peptide vaccine, development of a formulation that is efficient and safe is strongly desired.

Non-patent reference 1: Schenk D, Barbour R, Dunn W, Gordon G, Grajeda H, Guido T, et al., Immunization with amyloid-beta attenuates Alzheimer disease-disease-like pathology in the PDAPP mouse. Nature 1999; 400: p. 173-177

Non-patent reference 2: Fox N C, Black R S, Gilman S, Rossor M N, Griffith S G, Jenkins L, et al. Effects of A beta immunization (AN1792) on MRI measures of cerebral volume in Alzheimer disease. Neurology 2005; 64: p. 1563-1572

Non-patent reference 3: Nicoll J A, Wilkinson D, Holmes C, Steart P, Markham H, Weller R O. Neuropathology of human Alzheimer disease after immunization with amyloid-beta peptide: a case report. Nat Med 2003; 9: p. 448-452

DISCLOSURE OF THE INVENTION

Technical Problem to be Solved by the Invention

As mentioned above, there is a concern that the substances known to have an adjuvant effect may exert adverse side effects contrary to the adjuvant effect. Thus, an object of the present invention is to provide a novel method for enhancing an immune response using a substance which has already been confirmed to be safe for the living body and an immunogenic peptide that induces an enhanced immune response for use in said method.

Means for Solving the Problems

The present inventors have earnestly investigated a method for immunization and for enhancing immunization that is safe for the living body, efficacious and inexpensive, and as a result, have found that a capacity of inducing an enhanced immune response of a peptide of interest may be enhanced by addition or insertion of a cysteine residue, an amino acid constituting a naturally-occurring protein, to thereby accomplish the present invention.

The present invention relates to a method of enhancing an immune response inducing property of a peptide derived from Aβ, which is a causative substance of Alzheimer disease, or a portion thereof, characterized by addition or insertion of cysteine to Aβ peptide or a portion thereof. The present invention includes the followings:

(1) An immunogenic peptide that induces an enhanced immune response comprising an amyloid β peptide or a portion thereof with addition or insertion of cysteine or with addition of a peptide containing cysteine;

(2) The immunogenic peptide according to the above (1) wherein cysteine is added at the N-terminal or the C-terminal or both of the amyloid β peptide or a portion thereof;

(3) The immunogenic peptide according to the above (1) or (2) wherein cysteine is added at the C-terminal of the amyloid β peptide or a portion thereof;

(4) The immunogenic peptide according to any of the above (1) to (3) wherein 1 or 2 molecules of cysteine are added;

(5) The immunogenic peptide according to the above (1) wherein the peptide containing cysteine is added at the C-terminal of the amyloid β peptide or a portion thereof;

(6) The immunogenic peptide according to the above (1) wherein cysteine is inserted into the amyloid β peptide or a portion thereof;

(7) The immunogenic peptide according to the above (6) wherein cysteine is inserted between the 18th and 19th amino acid residues, between the 25th and 26th amino acid residues, or between the 28th and 29th amino acid residues counted from the N-terminus of an amyloid β peptide or a portion thereof;

(8) The immunogenic peptide according to any of the above (1) to (7) wherein the amyloid β peptide or a portion thereof consists of the amino acid sequence of SEQ ID NO: 34 or a portion thereof;

(9) The immunogenic peptide according to any of the above (1) to (8) which consists of an amino acid sequence selected from the group consisting of SEQ ID NO: 6, SEQ ID NO: 8, SEQ ID NO: 12, SEQ ID NO: 21, SEQ ID NO: 23, SEQ ID NO: 29, SEQ ID NO: 32, SEQ ID NO: 38, SEQ ID NO: 40, SEQ ID NO: 42, SEQ ID NO: 46, SEQ ID NO: 48, SEQ ID NO: 50, SEQ ID NO: 52, SEQ ID NO: 54 and SEQ ID NO: 56;

(10) A medicament for preventing or treating Alzheimer disease which comprises as an active ingredient the immunogenic peptide of any of the above (1) to (9);

(11) A medicament for preventing or treating Alzheimer disease which comprises as an active ingredient the immunogenic peptide of any of the above (1) to (9) together with an adjuvant;

(12) A DNA vaccine effective for preventing or treating Alzheimer disease which comprises a gene fragment encoding the amino acid sequence of the immunogenic peptide of any of the above (1) to (9);

(13) A method for enhancing an immune response which comprises using an immunogenic peptide that induces an enhanced immune response comprising an amyloid β peptide or a portion thereof with addition or insertion of cysteine or with addition of a peptide containing cysteine;

(14) A method for enhancing an immune response which comprises using an immunogenic peptide that induces an enhanced immune response comprising an amyloid β peptide or a portion thereof with addition or insertion of cysteine or with addition of a peptide containing cysteine together with an adjuvant;

(15) A method for enhancing an immune response which comprises using as a DNA vaccine a vector containing a gene fragment encoding an amino acid sequence of an immunogenic peptide that induces an enhanced immune response comprising an amyloid β peptide or a portion thereof with addition or insertion of cysteine or with addition of a peptide containing cysteine.

EFFECTS OF THE INVENTION

The present invention provides an immunogenic peptide that induces an enhanced and sufficient immune response even if it is used alone without an adjuvant. According to the present invention, merely by addition or insertion of cysteine residues to the amyloid β peptide or a portion thereof, antibody production of an immunogenic peptide may be enhanced. Therefore, there is no disadvantage associated with the use of an adjuvant to allow for easier design of a drug formulation.

The immunogenic peptide of the present invention that induces an enhanced immune response, when administered to the living body, may rapidly and abundantly induce an antibody specific to the peptide in blood. No toxicity of cysteine is known but rather cysteine and its related substances are known to have an antitoxic effect in the living body and therefore the immunogenic peptide of the present invention that induces an enhanced immune response may be used in the body very safely.

The immunogenic peptide of the present invention that induces an enhanced immune response, when used as a peptide vaccine, may be the simplest vaccine comprising as an active ingredient only the immunogenic peptide with addition or insertion of cysteine. Such immunogenic peptide with addition or insertion of cysteine may be prepared by chemical synthesis without biological synthesis and hence in higher uniformity than the conventional component vaccines. Additionally, with the lowest risk of toxicity, infection and decrease in quality due to contamination, a safer vaccine may be provided.

A peptide preparation comprising the immunogenic peptide of the present invention that induces an enhanced immune response may be administered not only by injection such as subcutaneous or intramuscular administration but also by oral, transnasal or transdermal administration, which would avoid stress and medical accidents caused by syringe needle.

BEST MODE FOR CARRYING OUT THE INVENTION

For preparing the immunogenic peptide of the present invention that induces an enhanced immune response, a cysteine residue may be added or inserted to the Aβ peptide or a portion thereof or alternatively a nucleotide sequence encoding cysteine may be added or inserted to the DNA or RNA sequence of the Aβ peptide or a portion thereof for expression. With respect to the position of addition or insertion of cysteine in the Aβ peptide or a portion thereof, in the case of addition, cysteine may be added at the N-terminal or the C-terminal or both of the peptide and, in the case of insertion, cysteine may be inserted at any position in the peptide. Addition at the C-terminal of the peptide is preferable wherein 1 or 2 cysteine residue(s) may be added. However, insofar as the immune response enhancing effect may be obtained, the position of addition and insertion or the number of cysteine residues are not especially limited. In another aspect of the present invention, a peptide containing cysteine, in place of cysteine, may also be added at the C-terminal of the peptide.

The Aβ peptide consists of 42 amino acid residues (Aβ42) and has the following amino acid sequence:

```
                                          (SEQ ID NO: 34)
DAEFRHDSGYEVHHQKLVFFAEDVGSNKGAIIGLMVGGVVIA.
```

Cysteine (Cys) may be added or inserted to the Aβ peptide or a portion thereof to provide the immunogenic peptide of the present invention that induce an enhanced immune response. A portion of the Aβ peptide includes those consisting of an amino acid sequence comprising at least the 1st-28th of the aforementioned amino acid sequence of Aβ42. Alternatively, a peptide containing cysteine may be added to the Aβ peptide or a portion thereof. The thus obtained immunogenic peptide that induces an enhanced immune response is efficacious for preventing or treating Alzheimer disease.

Specifically, a preferred example of the immunogenic peptide of the present invention that induces an enhanced immune response includes the following Aβ peptides with addition or insertion of cysteine wherein an added or inserted cysteine residue is underlined.

(1) Peptide with addition of 1 molecule at the C-terminal:

```
28AACys:
                                          (SEQ ID NO: 6)
DAEFRHDSGYEVHHQKLVFFAEDVGSNKC
```

-continued
```
29AACys:
                                          (SEQ ID NO: 8)
DAEFRHDSGYEVHHQKLVFFAEDVGSNKGC 30AACys:
                                          (SEQ ID NO: 10)
DAEFRHDSGYEVHHQKLVFFAEDVGSNKGAC 31AACys:
                                          (SEQ ID NO: 12)
DAEFRHDSGYEVHHQKLVFFAEDVGSNKGAIC 35AACys:
                                          (SEQ ID NO: 21)
DAEFRHDSGYEVHHQKLVFFAEDVGSNKGAIIGLMC 36AACys:
                                          (SEQ ID NO: 23)
DAEFRHDSGYEVHHQKLVFFAEDVGSNKGAIIGLMVC 37AACys:
                                          (SEQ ID NO: 25)
DAEFRHDSGYEVHHQKLVFFAEDVGSNKGAIIGLMVGC 38AACys:
                                          (SEQ ID NO: 27)
DAEFRHDSGYEVHHQKLVFFAEDVGSNKGAIIGLMVGGC 39AACys:
                                          (SEQ ID NO: 29)
DAEFRHDSGYEVHHQKLVFFAEDVGSNKGAIIGLMVGGVC 40AACys:
                                          (SEQ ID NO: 32)
DAEFRHDSGYEVHHQKLVFFAEDVGSNKGAIIGLMVGGVVC 42AACys:
                                          (SEQ ID NO: 36)
DAEFRHDSGYEVHHQKLVFFAEDVGSNKGAIIGLMVGGVVIAC
```

(2) Peptide with addition of 2 molecules at the C-terminal:

```
28AACysCys:
DAEFRHDSGYEVHHQKLVFFAEDVGSNKCC (SEQ ID NO: 38)
```

(3) Peptide with addition of 1 molecule at the N-terminal:

```
Cys28AA:
CDAEFRHDSGYEVHHQKLVFFAEDVGSNK    (SEQ ID NO: 40)
```

(4) Peptide with addition of each 1 molecule at the C-terminal and the N-terminal:

```
Cys28AACys:
CDAEFRHDSGYEVHHQKLVFFAEDVGSNKC  (SEQ ID NO: 42)
```

(5) Peptide with insertion of 1 molecule:

```
28AA18Cys:
                                          (SEQ ID NO: 46)
DAEFRHDSGYEVHHQKLVCFFAEDVGSNK

28AA25Cys:
                                          (SEQ ID NO: 48)
DAEFRHDSGYEVHHQKLVFFAEDVGCSNK

33AA28Cys:
                                          (SEQ ID NO: 50)
DAEFRHDSGYEVHHQKLVFFAEDVGSNKCGAIIG

35AA28Cys:
                                          (SEQ ID NO: 52)
DAEFRHDSGYEVHHQKLVFFAEDVGSNKCGAIIGLM
```

(6) Peptide with addition of 1 molecule at the C-terminal+ addition of an exogenous peptide (the exogenous peptide is positioned at the C-terminal of the added cysteine residue):

```
28AACysTTD:
                                           (SEQ ID NO: 54)
DAEFRHDSGYEVHHQKLVFFAEDVGSNKCTTD

28AACysEIFEFTTD:
                                           (SEQ ID NO: 56)
DAEFRHDSGYEVHHQKLVFFAEDVGSNKCEIFEFTTD
```

Among the Aβ peptides with addition or insertion of cysteine aforementioned, 28-amino acid Aβ peptide with addition of cysteine (28AACys: SEQ ID NO: 6), 29-amino acid Aβ peptide with addition of cysteine (29AACys: SEQ ID NO: 8), 31-amino acid Aβ peptide with addition of cysteine (31AACys: SEQ ID NO: 12), 35-amino acid Aβ peptide with addition of cysteine (35AACys: SEQ ID NO: 21), 36-amino acid Aβ peptide with addition of cysteine (36AACys: SEQ ID NO: 23), 39-amino acid Aβ peptide with addition of cysteine (39AACys: SEQ ID NO: 29), 40-amino acid Aβ peptide with addition of cysteine (40AACys: SEQ ID NO: 32), 42-amino acid Aβ peptide with addition of cysteine (42AACys: SEQ ID NO: 36), 28-amino acid Aβ peptide with addition of 2 cysteines at the C-terminal (28AACysCys: SEQ ID NO: 38) and 28-amino acid Aβ peptide with insertion of cysteine between 18th-19th amino acid residues (28AA18Cys: SEQ ID NO: 46) could particularly induce the enhanced immune response and thus may be used to prevent or treat Alzheimer disease efficaciously.

According to the present invention, a peptide that induces an enhanced immune response may be prepared by adding cysteine at the N-terminal, the C-terminal, or both of the N-terminal and the C-terminal of the Aβ peptide or a portion thereof or by inserting cysteine into said peptide. Whether a peptide obtained after addition or insertion of cysteine exerts an immune response-enhancing effect may be corroborated by immunization of mice with the peptide using the conventional techniques and determining an anti-Aβ IgG antibody titer in blood. Thus, the present invention also provides a method of preparing an immunogenic peptide that induces an enhanced immune response characterized by adding one or more cysteines at the N-terminal, the C-terminal, or both at the N-terminal and the C-terminal of the Aβ peptide or a portion thereof or inserting one or more cysteines to the peptide, immunizing an animal with the resulting peptide, and then determining an anti-Aβ IgG antibody titer in blood of the animal.

A peptide preparation containing the immunogenic peptide of the present invention that has an enhanced immune response-inducing property may be administered by any route of administration such as subcutaneous, transdermal, intramuscular, oral, or transnasal.

While the immunogenic peptide of the present invention that induces an enhanced immune response may provide sufficient immunization even if it is administered alone without an adjuvant, it may provide further sufficient immunization if in combination with an adjuvant. It will thus become possible to select various types of adjuvants such as e.g. an adjuvant attached importance to an effect of enhancing immunization or an adjuvant attached importance to a safety.

Moreover, a vector which comprises a gene fragment encoding each of the immunogenic peptides of the present invention as listed above that induce an enhanced immune response obtained by addition or insertion of cysteine to the Aβ peptide or a portion thereof may be used as a DNA vaccine for efficaciously preventing and treating Alzheimer disease. A nucleotide sequence encoding cysteine includes e.g. tgt but may be any sequence as far as it encodes cysteine. A gene fragment encoding the amino acid sequence of the Aβ peptide (Aβ42) consisting of the 42 amino acid residues mentioned above (SEQ ID NO: 34) is described below. However, the nucleotide sequence described below represents a typical gene sequence of the Aβ peptide but any gene sequence may be employed insofar as it encodes the same amino acid sequence.

```
                                           (SEQ ID NO: 35)
gatgcagaat tccgacatga ctcaggatat gaagttcatc atcaaaaatt ggtgttcttt gcagaagatg tgggttcaaa caaaggtgca atcattggac tcatggtggg cggtgttgtc atagcg
```

An example of a gene fragment encoding each of the immunogenic peptides of the present invention as listed above that induce an enhanced immune response obtained by addition or insertion of cysteine to the Aβ peptide or a portion thereof includes those described below. However, the nucleotide sequences described below represent a typical gene sequence encoding each of the peptides mentioned above but any gene sequence may be employed insofar as it encodes the same amino acid sequence.

```
Gene fragment encoding 26AACys:
                                           (SEQ ID NO: 2)
gatgcagaat tccgacatga ctcaggatat gaagttcatc atcaaaaatt ggtgttcttt gcagaagatg tgggttcatgt Gene fragment encoding 27AACys:
                                           (SEQ ID NO: 4)
gatgcagaat tccgacatga ctcaggatat gaagttcatc atcaaaaatt ggtgttcttt gcagaagatg tgggttcaaa ctgt Gene fragment encoding 28AACys:
                                           (SEQ ID NO: 7)
gatgcagaat tccgacatga ctcaggatat gaagttcatc atcaaaaatt ggtgttcttt gcagaagatg tgggttcaaa caaatgt Gene fragment encoding 29AACys:
                                           (SEQ ID NO: 9)
gatgcagaat tccgacatga ctcaggatat gaagttcatc atcaaaaatt ggtgttcttt gcagaagatg tgggttcaaa caaaggttgt Gene fragment encoding 30AACys:
                                           (SEQ ID NO: 11)
gatgcagaat tccgacatga ctcaggatat gaagttcatc atcaaaaatt ggtgttcttt gcagaagatg tgggttcaaa caaaggtgca tgt Gene fragment encoding 31AACys:
                                           (SEQ ID NO: 13)
gatgcagaat tccgacatga ctcaggatat gaagttcatc atcaaaaatt ggtgttcttt gcagaagatg tgggttcaaa caaaggtgca atctgt
```

-continued

Gene fragment encoding 32AACys:
(SEQ ID NO: 15)
gatgcagaat tccgacatga ctcaggatat gaagttcatc atcaaaaatt ggtgttcttt gcagaagatg tgggttcaaa caaaggtgca atcatttgt Gene fragment encoding 33AACys:
(SEQ ID NO: 17)
gatgcagaat tccgacatga ctcaggatat gaagttcatc atcaaaaatt ggtgttcttt gcagaagatg tgggttcaaa caaaggtgca atcattggat gt Gene fragment encoding 34AACys:
(SEQ ID NO: 19)
gatgcagaat tccgacatga ctcaggatat gaagttcatc atcaaaaatt ggtgttcttt gcagaagatg tgggttcaaa caaaggtgca atcattggac tctgt Gene fragment encoding 35AACys:
(SEQ ID NO: 22)
gatgcagaat tccgacatga ctcaggatat gaagttcatc atcaaaaatt ggtgttcttt gcagaagatg tgggttcaaa caaaggtgca atcattggac tcatgtgt Gene fragment encoding 36AACys:
(SEQ ID NO: 24)
gatgcagaat tccgacatga ctcaggatat gaagttcatc atcaaaaatt ggtgttcttt gcagaagatg tgggttcaaa caaaggtgca atcattggac tcatggtgtg t Gene fragment encoding 37AACys:
(SEQ ID NO: 26)
gatgcagaat tccgacatga ctcaggatat gaagttcatc atcaaaaatt ggtgttcttt gcagaagatg tgggttcaaa caaaggtgca atcattggac tcatggtggg ctgt Gene fragment encoding 38AACys:
(SEQ ID NO: 28)
gatgcagaat tccgacatga ctcaggatat gaagttcatc atcaaaaatt ggtgttcttt gcagaagatg tgggttcaaa caaaggtgca atcattggac tcatggtggg cggttgt Gene fragment encoding 39AACys:
(SEQ ID NO: 30)
gatgcagaat tccgacatga ctcaggatat gaagttcatc atcaaaaatt ggtgttcttt gcagaagatg tgggttcaaa caaaggtgca atcattggac tcatggtggg cggtgtttgt Gene fragment encoding 40AACys:
(SEQ ID NO: 33)
gatgcagaat tccgacatga ctcaggatat gaagttcatc atcaaaaatt ggtgttcttt gcagaagatg tgggttcaaa caaaggtgca atcattggac tcatggtggg cggtgttgtc tgt Gene fragment encoding 42AACys:
(SEQ ID NO: 37)
gatgcagaat tccgacatga ctcaggatat gaagttcatc atcaaaaatt ggtgttcttt gcagaagatg tgggttcaaa caaaggtgca atcattggac tcatggtggg cggtgttgtc atagcgtgt Gene fragment encoding 28AACysCys:
(SEQ ID NO: 39)
gatgcagaat tccgacatga ctcaggatat gaagttcatc atcaaaaatt ggtgttcttt gcagaagatg tgggttcaaa caaatgttgt Gene fragment encoding Cys28AA:
(SEQ ID NO: 41)
tgtgatgcag aattccgaca tgactcagga tatgaagttc atcatcaaaa attggtgttc tttgcagaag atgtgggttc aaacaaa Gene fragment encoding Cys28AACys:
(SEQ ID NO: 43)
tgtgatgcag aattccgaca tgactcagga tatgaagttc atcatcaaaa attggtgttc tttgcagaag atgtgggttc aaacaaatgt Gene fragment encoding 28AA18Cys:
(SEQ ID NO: 47)
gatgcagaat tccgacatga ctcaggatat gaagttcatc atcaaaaatt ggtgtgtttc tttgcagaag atgtgggttc aaacaaa Gene fragment encoding 28AA25Cys:
(SEQ ID NO: 49)
gatgcagaat tccgacatga ctcaggatat gaagttcatc atcaaaaatt ggtgttcttt gcagaagatg tgggtgttcaaa caaa Gene fragment encoding 33AA28Cys:
(SEQ ID NO: 51)
gatgcagaat tccgacatga ctcaggatat gaagttcatc atcaaaaatt ggtgttcttt gcagaagatg tgggttcaaa caaatgtggt gcaatcattg ga Gene fragment encoding 35AA28Cys:
(SEQ ID NO: 53)
gatgcagaat tccgacatga ctcaggatat gaagttcatc atcaaaaatt ggtgttcttt gcagaagatg tgggttcaaa caaatgtggt gcaatcattg gactcatg Gene fragment encoding 28AACysTTD (SEQ ID NO: 54):
(SEQ ID NO: 55)
gatgcagaat tccgacatga ctcaggatat gaagttcatc atcaaaaatt ggtgttcttt gcagaagatg tgggttcaaa caaatgtact actgac Gene fragment encoding
28AACysEIFEFTTD (SEQ ID NO: 56):
(SEQ ID NO: 57)
gatgcagaat tccgacatga ctcaggatat gaagttcatc atcaaaaatt ggtgttcttt gcagaagatg tgggttcaaa caaatgtgaa atcttcgaat tcactactga c The present invention is explained in more detail by means of the following Examples but should not be construed to be limited thereto.

EXAMPLE 1

Comparison Of Antibody Inducing Ability Between Aβ Peptides With And Without Addition Of Cysteine (1) Preparation of Aβ Peptides with Addition of Cysteine

28AA:
(SEQ ID NO: 5)
DAEFRHDSGYEVHHQKLVFFAEDVGSNK

28AACys:
(SEQ ID NO: 6)
DAEFRHDSGYEVHHQKLVFFAEDVGSNKC

35AA:
(SEQ ID NO: 20)
DAEFRHDSGYEVHHQKLVFFAEDVGSNKGAIIGLM

35AACys:
(SEQ ID NO: 21)
DAEFRHDSGYEVHHQKLVFFAEDVGSNKGAIIGLMC

The above peptides were synthesized (Hokkaido System Science Co., Ltd.) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 16 mice were divided into 4 groups each comprising 4 mice: Group 1 administered with 28AA; Group 2 administered with 28AACys; Group 3 administered with 35AA; and Group 4 administered with 35AACys.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 of the 2nd immunization, 50 to 150 μL of blood was collected from the tail vein. Further, on Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Measurement of Anti-Aβ IgG Antibody

The Aβ peptide (1-40 amino acid sequence: DAEFRHDS-GYEVHHQKLVFFAEDVGSNKGAIIGLMVGGVV (SEQ ID NO: 31) synthesized by Hokkaido System Science Co., Ltd.), diluted to 10 μg/mL with 0.1M carbonate buffer, pH9.6, was added to 8-well strips (Nalge Nunc K.K., Immobilizer Amino) at 100 μL/well and left to incubate at 4° C. overnight for immobilization. On the following day, each well was washed 3 times with 300 μL of PBS containing 0.05% Tween20 (PBST), added with 10 mM ethanolamine at 300 μL/well and left to incubate at room temperature for 1 hour.

After 1 hour, the 10 mM ethanolamine was fully removed and a specimen diluted with PBST by 50- to 10000-fold was added to each well at 100 μL/well. After reaction at room temperature for 1 hour, the diluted serum added was discarded and each well was washed 3 times with 300 μL/well of PBST. After washing, the wash solution in the well was fully removed, an HRP-labeled anti-mouse IgG goat antibody (American Curlex, A131PS) diluted with the solution for the specimen dilution by 2000-fold was added at 100 μL/well followed by reaction at room temperature for 1 hour. After the reaction, the solution for labeled antibody dilution was discarded and each well was washed twice with 300 μL/well of PBST and twice with the equivalent amount of distilled water, to which 100 μL/well of a chromogenic substrate solution TMB+ (Dako Inc.) was added followed by reaction at room temperature for 30 min. under shading. Then, 100 μL/well of 1N sulfuric acid was added to quench development and optical density at 450 nm (OD450 value) was measured.

A commercially available monoclonal antibody to Aβ (CHEMI-CON Corporation, MAB1560) was used as standard serum. The standard serum was diluted with PBST to 0.156, 0.3125, 0.625, 1.25, 2.5, 5, 10 ng/mL to prepare standards for the antibody titer measurement. An anti-Aβ IgG antibody of each murine serum specimen was determined and simultaneously the OD450 value of each diluted specimen was measured. An anti-Aβ IgG antibody titer of each murine serum specimen was calculated using the unit of the resulting standards and the standard curve of the OD450 value.

Table 1 shows the calculated anti-Aβ antibody titer of the murine serum in each of the immunization groups. As shown in Table 1, as compared to the immunization with Aβ peptide fragments without addition of cysteine (28AA, 35AA), the immunization with Aβ peptide fragments with addition of cysteine (28AACys, 35AACys) provided a higher antibody titer against Aβ. Increase in the antibody titer was observed for the 28AA with addition of cysteine by about 39-fold and for the 35AA with addition of cysteine by about 26-fold.

Table 1

| | | Antibody titer (ng/mL) | |
|---|---|---|---|
| Group | Animal No. | Day 7 from 3rd administration | Day 7 from 2nd administration |
| 28AA | 1 | 216.6 | 35.1 |
| | 2 | 149.7 | 21.0 |
| | 3 | 2531.0 | 5075.0 |
| | 4 | 79.9 | 10851.0 |
| | Mean | 744.30 | 3995.53 |
| 28AACys | 1 | 20265.0 | 74096.0 |
| | 2 | 2337.0 | 30542.0 |
| | 3 | 69198.0 | 389239.0 |
| | 4 | 12372.0 | 137192.0 |
| | Mean | 26043.00 | 157767.25 |
| 35AA | 1 | 78.7 | 34.4 |
| | 2 | 435.2 | 3584.0 |
| | 3 | 236.2 | 1745.0 |
| | 4 | 409.5 | 23739.0 |
| | Mean | 289.90 | 7275.60 |
| 35AACys | 1 | 3231.0 | 382533.0 |
| | 2 | 3240.0 | 37390.0 |
| | 3 | 3237.0 | 88795.0 |
| | 4 | 3237.0 | 257920.0 |
| | Mean | 3236.25 | 191659.50 |

EXAMPLE 2

Comparison Of Antibody Inducing Ability Between Aβ Peptide With Addition Of Cysteine And Carrier-Linked Aβ Peptide (With/Without Adjuvant)

(1) Preparation of Aβ peptide with addition of cysteine and carrier-linked Aβ peptide 28AACys:
(SEQ ID NO: 6)
DAEFRHDSGYEVHHQKLVFFAEDVGSNKC

28AA-KLH:
(SEQ ID NO: 58)
DAEFRHDSGYEVHHQKLVFFAEDVGSNK-C-KLH

The above peptides were synthesized (KITAYAMA LABES Co., Ltd.) and diluted with saline to obtain a 1 mg/mL stock solution which was stored at −80° C. or lower till use. KLH (keyhole limpet hemocyanin) is a carrier protein of 60 kDa. Cys in the 28AA-KLH was used as a linker to combine the 28AA peptide with KLH and was not intended to enhance the immune response effect. To combine a carrier protein with the immunogenic peptide using Cys is a routine method for peptide immunization.

(2) Adjuvant

Freund's complete adjuvant (hereafter referred to as "FCA"), Freund's incomplete adjuvant (hereafter referred to as "FICA"), (GERBU, #1841, #1842), Gerbu adjuvant MM (GERBU, #3001.0106) and Alhydrogel '85' 2% (Brenntag) which were commercially available were used as adjuvants.

(3) Administered Mice

Male C57BL/6 mice (9 weeks old, SPF) were purchased from Japan Charles River Cc., Ltd. and bred in SPF environment.

(4) Immunization Groups

The 25 mice were divided into 5 groups each comprising 5 mice: Group 1 administered with 28AACys; Group administered with 28AA-KLH; Group 3 administered with 28AA-KLH +FCA/FICA; Group 4 administered with 28AA-KLH+ Gerbu adjuvant MM; and Group 5 administered with 28AA-KLH+Alhydrogel '85' 2%.

(5) Dose and Preparation of Sample for Administration

A primary dose of Aβ peptide was 100 μg per animal, and second and third doses were 50 μg per animal. Namely, to prepare the primary dose for the group administered with 28AACys, 0.5 mL of 28AACys and 0.5 mL of saline were mixed, and to prepare the second and third doses, 0.25 mL of 28AACys and 0.75 mL of saline were mixed. To prepare the primary dose for the group administered with 28AA-KLH, 0.5 mL of 28AA-KLH and 0.5 mL of saline were mixed, and to prepare the second and third doses, 0.25 mL of 28AA-KLH and 0.75 mL of saline were mixed. To prepare the primary dose for the group administered with 28AA-KLH+FCA/FICA, 0.5 mL of 28AA-KLH and 0.5 mL of FCA were mixed to be emulsified, and to prepare the second and third doses, 0.25 mL of 28AA-KLH, 0.25 mL of saline and 0.5 mL of FICA were mixed to be emulsified. To prepare the primary dose for the group administered with 28AA-KLH+Gerbu adjuvant MM, 0.5 mL of 28AA-KLH, 0.4 mL of saline and 0.1 mL of Gerbu adjuvant MM were mixed, and to prepare the second and third doses, 0.25 mL of 28AA-KLH, 0.65 mL of saline and 0.1 mL of Gerbu adjuvant MM were mixed. To prepare the first dosage for the group administered with 28AA-KLH+Alhydrogel '85' 2%, 0.5 mL of 28AA-KLH and 0.5 mL of Alhydrogel '85' 2% were mixed, and to prepare the second and third doses, 0.25 mL of 28AA-KLH, 0.25 mL of saline and 0.5 mL of Alhydrogel '85' 2% were mixed.

(6) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(7) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(8) Measurement of Anti-Aβ IgG Antibody

Measurement of the anti-Aβ IgG antibody was conducted as described above. Table 2 shows the calculated anti-Aβ antibody titer of the murine serum in each of the immunization groups. As shown in Table 2, the Aβ peptide fragment with addition of a carrier KLH together with Freund's complete/incomplete adjuvant provided the highest antibody titer against Aβ. The secondly highest antibody titer was provided by the Aβ peptide fragment with addition of cysteine, which was significantly higher than those of using as a adjuvant Gerbu adjuvant MM (GERBU) or Alhydrogel '85' 2% or of the Aβ peptide fragment with addition of a carrier KLH.

Table 2

| | Antibody titer (ng/mL) | | | | | |
|---|---|---|---|---|---|---|
| | Animal No. | | | | | |
| Group | 1 | 2 | 3 | 4 | 5 | Mean |
| 1. 28AACys | 1714.4 | 5949.1 | 10122.3 | 716.6 | 2685.0 | 4237.48 |
| 2. 28AA-KLH | 47.8 | 33.9 | 430.4 | 42.7 | 42.2 | 119.40 |
| 3. 28AA-KLH + FCA/FICA | 12162.5 | 11484.1 | 12132.3 | 12161.9 | 2329.9 | 10054.14 |
| 4. 28AA-KLH + GERBU | 417.5 | 324.7 | 2846.0 | 3910.9 | 1774.3 | 1854.68 |
| 5. 28AA-KLH + ALHYDROGEL '85' 2% | 51.4 | 37.7 | 35.0 | 33.3 | 159.6 | 63.40 |

EXAMPLE 3

Comparison Of Antibody Inducing Ability Among Aβ peptides With Addition Of Cysteine Having 26-40 Amino Acid Sequence In Length (1) Preparation of Aβ Peptides with Addition of Cysteine

```
26AACys:
                                    (SEQ ID NO: 1)
DAEFRHDSGYEVHHQKLVFFAEDVGSC

27AACys:
                                    (SEQ ID NO: 3)
DAEFRHDSGYEVHHQKLVFFAEDVGSNC

28AACys:
                                    (SEQ ID NO: 6)
DAEFRHDSGYEVHHQKLVFFAEDVGSNKC

29AACys:
                                    (SEQ ID NO: 8)
DAEFRHDSGYEVHHQKLVFFAEDVGSNKGC

30AACys:
                                    (SEQ ID NO: 10)
DAEFRHDSGYEVHHQKLVFFAEDVGSNKGAC

31AACys:
                                    (SEQ ID NO: 12)
DAEFRHDSGYEVHHQKLVFFAEDVGSNKGAIC

32AACys:
                                    (SEQ ID NO: 14)
DAEFRHDSGYEVHHQKLVFFAEDVGSNKGAIIC

33AACys:
                                    (SEQ ID NO: 16)
DAEFRHDSGYEVHHQKLVFFAEDVGSNKGAIIGC

34AACys:
                                    (SEQ ID NO: 18)
DAEFRHDSGYEVHHQKLVFFAEDVGSNKGAIIGLC

35AACys:
                                    (SEQ ID NO: 21)
DAEFRHDSGYEVHHQKLVFFAEDVGSNKGAIIGLMC

36AACys:
                                    (SEQ ID NO: 23)
DAEFRHDSGYEVHHQKLVFFAEDVGSNKGAIIGLMVC

37AACys:
                                    (SEQ ID NO: 25)
DAEFRHDSGYEVHHQKLVFFAEDVGSNKGAIIGLMVGC

38AACys:
                                    (SEQ ID NO: 27)
DAEFRHDSGYEVHHQKLVFFAEDVGSNKGAIIGLMVGGC

39AACys:
                                    (SEQ ID NO: 29)
DAEFRHDSGYEVHHQKLVFFAEDVGSNKGAIIGLMVGGVC

40AACys:
                                    (SEQ ID NO: 32)
DAEFRHDSGYEVHHQKLVFFAEDVGSNKGAIIGLMVGGVVC
```

The above peptides were synthesized (Hokkaido System Science Co., Ltd.) and diluted with saline to obtain a 5 mg/mL stock solution. To 100 µL of the stock solution was added 900 µL of saline to 0.5 mg/mL of the concentration and the mixture was dispensed into 1.5 mL tube (immunogen) and stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 60 mice were divided into 15 groups each comprising 4 mice: Group 1 administered with 26AACys; Group 2 administered with 27AACys; Group 3 administered with 28AACys; Group 4 administered with 29AACys; Group 5 administered with 30AACys; Group 6 administered with 31AACys; Group 7 administered with 32AACys; Group 8 administered with 33AACys; Group 9 administered with 34AACys; Group 10 administered with 35AACys; Group 11 administered with 36AACys; Group 12 administered with 37AACys; Group 13 administered with 38AACys; Group 14 administered with 39AACys; and Group 15 administered with 40AACys.

(4) Immunization and Schedule

Each 200 µL/mouse of an immunogen was administered to mice using a 1 mL tuberculin syringe (Terumo, SS-01T2613S) intradermally or subcutaneously at the abdomen (dose per mouse: 100 µg). The mice were immunized 3 times at 2-week intervals.

(5) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Measurement of Anti-Aβ IgG Antibody

Measurement of the anti-Aβ IgG antibody was conducted as described above. Table 3 shows the calculated anti-β antibody titer of the murine serum in each of the immunization groups. As shown in Table 3, it was observed that, among the groups administered with Aβ peptides with addition of cysteine which have 26 to 40 amino acid residues in length, those with 28 or more amino acid residues in length had the antibody inducing ability against Aβ. In particular, 28AACys, 29AACys, 31AACys, 35AACys, 36AACys, 39AACys, and 40AACys showed the higher antibody titer.

Table 3

| | Antibody titer (ng/mL) | | | | |
| --- | --- | --- | --- | --- | --- |
| | Animal No. | | | | |
| Group | 1 | 2 | 3 | 4 | Mean |
| 1. 26AACys | 39 | 19 | 21 | 19 | 24.5 |
| 2. 27AACys | 15 | 19 | 24 | 19 | 19.9 |
| 3. 28AACys | 3120 | 2191 | 115618 | 86736 | 51916.1 |
| 4. 29AACys | 143754 | 5545 | 74235 | 114322 | 84464.2 |
| 5. 30AACys | 10706 | 72 | 7335 | 1414 | 4881.5 |
| 6. 31AACys | 110312 | 377757 | 5809 | 51904 | 136445.4 |
| 7. 32AACys | 27 | 18 | 213 | 19 | 69.4 |
| 8. 33AACys | 44 | 28 | 35 | 27 | 33.4 |
| 9. 34AACys | 24 | 25 | 74 | 18 | 35.3 |
| 10. 35AACys | 382533 | 37390 | 88795 | 257920 | 191659.5 |
| 11. 36AACys | 36535 | 16261 | 44439 | 13262 | 27624.4 |
| 12. 37AACys | 228 | 3003 | 2763 | 1051 | 1761.1 |
| 13. 38AACys | 4936 | 952 | 478 | 4371 | 2684.3 |
| 14. 39AACys | 447512 | 196147 | 85137 | 13445 | 185560.2 |
| 15. 40AACys | 22998 | 15192 | 204464 | 25604 | 67041.8 |

EXAMPLE 4

Comparison Of Antibody Inducing Ability Among Aβ Peptides Without Addition Of Cysteine, With Addition Of 1 Molecule Of Cysteine And With Addition Of 2 Molecules Of Cysteine (1) Preparation of Aβ Peptides without and with Addition of Cysteine.

```
28AA:
                               (SEQ ID NO: 5)
DAEFRHDSGYEVHHQKLVFFAEDVGSNK

28AACys:
                               (SEQ ID NO: 6)
DAEFRHDSGYEVHHQKLVFFAEDVGSNKC

28AACysCys:
                               (SEQ ID NO: 38)
DAEFRHDSGYEVHHQKLVFFAEDVGSNKCC
```

The above peptides were synthesized (Hokkaido System Science Co., Ltd.) and diluted with saline to obtain a 5 mg/mL stock solution, which was stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 12 mice were divided into 3 groups each comprising 4 mice: Group 1 administered with 28AA; Group 2 administered with 28AACys; and Group 3 administered with 28AACysCys.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 4th immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Measurement of Anti-Aβ IgG Antibody

Measurement of the anti-β IgG antibody was conducted as described above. Table 4 shows the calculated anti-Aβ antibody titer of the murine serum in each of the immunization Groups. As shown in Table 4, almost the same antibody inducing ability was found in the groups administered with 28AACys or 28AACysCys.

Table 4

| | Antibody titer (ng/mL) | | | | |
|---|---|---|---|---|---|
| | Animal No. | | | | |
| Group | 1 | 2 | 3 | 4 | Mean |
| 28AA | 69 | 54 | 67 | 42 | 58.0 |
| 28AACys | 211 | 365 | 19578 | 127 | 5070.2 |
| 28AACysCys | 139 | 19262 | 451 | 2928 | 5695.3 |

EXAMPLE 5

Comparison Of Antibody Inducing Ability Among Aβ Peptides With Addition Of Cysteine At The C-Terminal, The N-Terminal And Both Terminals (1) Preparation of Aβ Peptides with Addition of Cysteine

```
28AACys:
                               (SEQ ID NO: 6)
DAEFRHDSGYEVHHQKLVFFAEDVGSNKC

Cys28AA:
                               (SEQ ID NO: 40)
CDAEFRHDSGYEVHHQKLVFFAEDVGSNK

Cys28AACys:
                               (SEQ ID NO: 42)
CDAEFRHDSGYEVHHQKLVFFAEDVGSNKC
```

The above peptides were synthesized (Hokkaido System Science Co., Ltd.) and diluted with saline to obtain a 5 mg/mL stock solution, which was stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 12 mice were divided into 3 groups each comprising 4 mice: Group 1 administered with 28AACys; Group 2 administered with Cys28AA; and Group 3 administered with Cys28AACys.

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(5) Blood Sampling

On Day 7 from the final 4th immunization, blood was collected from the abdominal aorta of all mice under anesthesia with pentobarbital sodium (Kyoritsu Seiyaku Corporation, Somnopentyl) and the mice were sacrificed. The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Measurement of Anti-Aβ IgG Antibody

Measurement of the anti-Aβ IgG antibody was conducted as described above. Table 5 shows the calculated anti-Aβ antibody titer of the murine serum in each of the immunization groups. As shown in Table 5, regardless of position of Cys addition, the antibody inducing ability was found in all the groups.

Table 5

| | Antibody titer (ng/mL) | | | | |
|---|---|---|---|---|---|
| | Animal No. | | | | |
| Group | 1 | 2 | 3 | 4 | Mean |
| 28AACys | 290461 | 94 | 139927 | 192986 | 155867.0 |
| Cys28AA | 7708 | 423 | 15328 | 108 | 5891.8 |
| Cys28AACys | 772 | 49849 | 1537 | 48 | 13051.8 |

EXAMPLE 6

Comparison Of Antibody Inducing Ability Among Aβ Peptide Sequences With Insertion Of Cysteine (1) Preparation of Aβ Peptides with Insertion of Cysteine

```
28AA7Cys:
                                        (SEQ ID NO: 44)
DAEFRHDCSGYEVHHQKLVFFAEDVGSNK

28AA10Cys:
                                        (SEQ ID NO: 45)
DAEFRHDSGYCEVHHQKLVFFAEDVGSNK

28AA18Cys:
                                        (SEQ ID NO: 46)
DAEFRHDSGYEVHHQKLVCFFAEDVGSNK

28AA25Cys:
                                        (SEQ ID NO: 48)
DAEFRHDSGYEVHHQKLVFFAEDVGCSNK

33AA28Cys:
                                        (SEQ ID NO: 50)
DAEFRHDSGYEVHHQKLVFFAEDVGSNKCGAIIG

35AA28Cys:
                                        (SEQ ID NO: 52)
DAEFRHDSGYEVHHQKLVFFAEDVGSNKCGAIIGLM

28AACys:
                                        (SEQ ID NO: 6)
DAEFRHDSGYEVHHQKLVFFAEDVGSNKC
```

The above peptides were synthesized (Sigma-Aldrich Japan K.K.) and diluted with saline to obtain a 5 mg/mL stock solution, which was stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 28 mice were divided into 7 groups each comprising 4 mice: Group 1 administered with 28AA7Cys; Group 2 administered with 28AA10Cys; Group 3 administered with 28AA18Cys; Group 4 administered with 28AA25Cys; Group 5 administered with 33AA28Cys; Group 6 administered with 35AA28Cys; and Group 7 administered with 28AACys.

(4) Immunization and Schedule

Each 200 µL/mouse of an immunogen was administered to mice using a 1 mL tuberculin syringe (Terumo, SS-01T2613S) intradermally or subcutaneously at the abdomen (dose per mouse: 100 µg). The mice were immunized 3 times at 2-week intervals.

(5) Blood Sampling

On Day 7 from the final 4th immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Measurement of Anti-Aβ IgG antibody

Measurement of the anti-Aβ IgG antibody was conducted as described above. Table 6 shows the calculated anti-Aβ antibody titer of the murine serum in each of the immunization Groups. As shown in Table 6, the antibody inducing ability was found in the groups administered with 28AA18Cys, 28AA25Cys, 33AA28Cys, 35AA28Cys or 28AACys. In particular, a higher antibody inducing ability was found for the group administered with 28AA18Cys, the 28 amino acids Aβ peptide with insertion of cysteine between the 18th and 19th amino acid residue, as compared to the group administered with 28AACys, the 28 amino acid Aβ peptide with addition of cysteine at the C-terminal.

Table 6

| Group | Antibody titer (ng/mL) Animal No. | | | | |
| --- | --- | --- | --- | --- | --- |
| | 1 | 2 | 3 | 4 | Mean |
| 28AA7Cys | 21 | 24 | 17 | 30 | 23.0 |
| 28AA10Cys | 26 | 19 | 18 | 8 | 17.7 |
| 28AA18Cys | 2163676 | 92083 | 54037 | 137801 | 611899.2 |
| 28AA25Cys | 14972 | 4721 | 4483 | 3267 | 6860.8 |
| 33AA28Cys | 245 | 1932 | 29 | 14214 | 4105.0 |
| 35AA28Cys | 1753 | 17265 | 2103 | 6469 | 6891.5 |
| 28AACys | 20883 | 10503 | 38907 | 5491 | 18946.0 |

EXAMPLE 7

Assessment Of Antibody Inducing Ability Of Aβ Peptide With Addition Of Cysteine Together With Addition Of Exogenous Amino Acid Sequence (Not Derived From Aβ Peptide)

(1) Preparation of Aβ Peptides with and without Addition of Cysteine

```
28AA:
                                        (SEQ ID NO: 5)
DAEFRHDSGYEVHHQKLVFFAEDVGSNK

28AACys:
                                        (SEQ ID NO: 6)
DAEFRHDSGYEVHHQKLVFFAEDVGSNKC

28AACysTTD:
                                        (SEQ ID NO: 54)
DAEFRHDSGYEVHHQKLVFFAEDVGSNKCTTD

28AACysEIFEFTTD:
                                        (SEQ ID NO: 56)
DAEFRHDSGYEVHHQKLVFFAEDVGSNKCEIFEFTTD
```

The above peptides were synthesized (Hokkaido System Science Co., Ltd.) and diluted with saline to obtain a 5 mg/mL stock solution, which was stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 16 mice were divided into 4 groups each comprising 4 mice: Group 1 administered with 28AA; Group 2 administered with 28AACys; Group 3 administered with 28AACysTTD (SEQ ID NO: 54); and Group 4 administered with 28AACysTTD (SEQ ID NO: 56).

(4) Immunization and Schedule

Each 200 µL/mouse of an immunogen was administered to mice using a 1 mL tuberculin syringe (Terumo, SS-01T2613S) intradermally or subcutaneously at the abdomen (dose per mouse: 100 µg). The mice were immunized 3 times at 2-week intervals.

(5) Blood Sampling

On Day 7 from the final 4th immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Measurement of anti-A,β IgG antibody

Measurement of the anti-A,β IgG antibody was conducted as described above. Table 7 shows the calculated anti-A,β antibody titer of the murine serum in each of the immunization Groups. As shown in Table 7, the antibody inducing ability was found in the groups administered with 28AACys (SEQ ID NO: 6), 28AACysTTD (SEQ ID NO: 54) or 28AACysEIFEFTTD (SEQ ID NO: 56). Thus, it was found that the antibody inducing ability of A,β sequence with addition of Cys remained even if an additional exogenous peptide sequence was bound to said A,β sequence.

Table 7

| | Antibody titer (ng/mL) | | | | |
|---|---|---|---|---|---|
| | Animal No. | | | | |
| Group | 1 | 2 | 3 | 4 | Mean |
| 28AA | 69 | 54 | 67 | 42 | 58.0 |
| 28AACys | 211 | 365 | 19578 | 127 | 5070.2 |
| 28AACysTTD | 46 | 108899 | 4316 | 1855 | 28279.3 |
| 28AACysEIFEFTTD | 8198 | 28782 | 2162 | 45257 | 21099.2 |

EXAMPLE 8

Nasal, Intradermal And Oral Administration Of Aβ Peptide With Addition Of Cysteine (1) Preparation of Aβ Peptide with Addition of Cysteine

```
35AACys:
                              (SEQ ID NO: 21)
DAEFRHDSGYEVHHQKLVFFAEDVGSNKGAIIGLMC
```

The above peptide was synthesized (Hokkaido System Science Co., Ltd.) and diluted with saline to obtain a 5 mg/mL stock solution, which was stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 9 mice were divided into 3 groups each comprising 3 mice: Group 1 nasally administered; Group 2 intradermally administered; and Group 3 orally administered.

(4) Immunization and Schedule
Primary Immunization

Common to each of Groups, to 200 μL of the stock solution was added 1800 μL of saline to 0.5 mg/mL of the concentration and 200 μL of the mixture was administered to mice using a 1 mL tuberculin syringe (Terumo, SS-01T2613S) intradermally or subcutaneously at the abdomen (dose per mouse: 100 μg). The 2nd, 3rd and 4th (final) immunizations of the mice of each group were conducted at weekly intervals after the primary immunization as described below.

Group 1: Nasal Administration

Each 20 μL of the stock solution was administered to mice via the nasal cavity using Pipetman P-20 (Gilson) (dose per mouse: 100 μg).

Group 2: Intradermal Administration

On the day before the administration the back of mice was shaved. Under anesthetization with isoflurane, the shaved area was disinfected with 70% alcohol and dried before administration and then 20 μL of the stock solution was administered dropwise to mice using Pipetman P-20 (Gilson) (dose per mouse: 100 μg).

Group 3: Oral administration

For the 2nd and 3rd immunizations, to 200 μL of the stock solution was added 2300 μL of saline to 0.2 mg/mL of the concentration and each 500 μL/mouse of the mixture was administered into the stomach of mice using a probe for oral use (Natsume Seisakusho CO LTD., KN-348, for mice) attached to a 1 mL tuberculin syringe (Terumo, SS-01T2613S) (dose per mouse: 200 μg). For the 4th (final) immunization, to 100 μL of the stock solution was added 2400 μL of saline to 0.2 mg/mL of the concentration and each 500 μL/mouse of the mixture was administered into the stomach of mice using a probe for oral use attached to a 1mL tuberculin syringe (dose per mouse: 100 μg).

(5) Blood Sampling

On Day 6 from the primary immunization, on Day 6 from the 2nd immunization and on Day 6 from the 3rd immunization, 50 to 150 μL of blood was collected from the tail vein. Further on Day 7 from the final 4th immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Measurement of Anti-Aβ IgG antibody

Measurement of the anti-Aβ IgG antibody was conducted as described above. Table 8 shows the calculated anti-Aβ antibody titer of the murine serum in each of the immunization Groups. As shown in Table 8, it was found that Aβ peptide fragment with addition of cysteine showed the antibody inducing ability against Aβ irrespective of nasal, percutaneous or oral administration.

Table 8

| | | Antibody titer (ng/mL) | | | |
|---|---|---|---|---|---|
| Group | Animal No. | Day 6 from primary administration | Day 6 from 2nd administration | Day 6 from 3rd administration | Day 6 from 4th administration |
| Nasal | 1 | 57.0 | 2564.0 | 19183.0 | 54669.0 |
| | 2 | 554.0 | 5707.0 | 20814.0 | 36128.0 |
| | 3 | 461.8 | 11773.0 | 10497.0 | 11895.0 |
| | Mean | 357.60 | 6681.33 | 16831.33 | 34230.67 |

-continued

| | | Antibody titer (ng/mL) | | | |
|---|---|---|---|---|---|
| Group | Animal No. | Day 6 from primary administration | Day 6 from 2nd administration | Day 6 from 3rd administration | Day 6 from 4th administration |
| Intradermal | 1 | 28.0 | 82.0 | 110.8 | 64.9 |
| | 2 | 13.6 | 1682.0 | 1746.0 | 1148.0 |
| | 3 | 293.2 | 2413.0 | 3809.0 | 11372.0 |
| | Mean | 111.80 | 1392.33 | 1888.60 | 4194.97 |
| Oral | 1 | 59.7 | 4412.0 | 4746.0 | 7301.0 |
| | 2 | 90.1 | 1526.0 | 1522.0 | 3396.0 |
| | 3 | 18.4 | 1960.0 | 1260.0 | 1752.0 |
| | Mean | 56.07 | 2632.67 | 2509.33 | 4149.67 |

EXAMPLE 9

Comparison Of Antibody Inducing Ability Of In Intradermal Administration Between Aβ Peptides With And Without Addition Of Cysteine (1) Preparation of Aβ Peptides with and without Addition of Cysteine

35AA:
(SEQ ID NO: 20)
DAEFRHDSGYEVHHQKLVFFAEDVGSNKGAIIGLM

35AACys:
(SEQ ID NO: 21)
DAEFRHDSGYEVHHQKLVFFAEDVGSNKGAIIGLMC

The above peptides were synthesized (Hokkaido System Science Co., Ltd.) and diluted with saline to obtain a 5 mg/mL stock solution, which was stored at −80° C. or lower till use.

(2) Immunized Mice

Male C57BL/6 mice (7 weeks old, SPF) were purchased from Japan Charles River Co., Ltd. and bred in SPF environment.

(3) Immunization Groups

The 10 mice were divided into 2 groups each comprising 5 mice: Group 1 administered with 35 amino acids Aβ peptide with addition of cysteine; and Group 2 administered with 35 amino acids Aβ peptide without addition of cysteine.

(4) Immunization and Schedule

The primary immunization was conducted as in Example 8. The 2nd, 3rd and 4th (final) immunizations were done at weekly intervals after the primary immunization as described below. On the day before the administration the back of mice was shaved. Under anesthetization with isoflurane, the shaved area was disinfected with 70% alcohol before administration, application/peeling-off of a surgical tape (Nichiban Co., Ltd.) was repeated 10 times to remove the corneal layer of epidermis and then 20 µL of the stock solution was administered dropwise to mice using Pipetman P-20 (Gilson) (dose per mouse: 100 µg).

(5) Blood Sampling

On Day 7 from the final 4th immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Measurement of Anti-Aβ IgG antibody

Measurement of the anti-Aβ IgG antibody was conducted as described above. Table 9 shows the calculated anti-Aβ antibody titer of the murine serum in each of the immunization Groups. As shown in Table 9, it was found that Aβ peptide fragment with addition of cysteine showed a higher antibody inducing ability by 10-fold or more as compared to Aβ peptide without addition of cysteine.

Table 9

| | Antibody titer (ng/mL) | | | | | |
|---|---|---|---|---|---|---|
| | Animal No. | | | | | |
| Group | 1 | 2 | 3 | 4 | 5 | Mean |
| 35AACys | 130292 | 21945 | 13948 | 83671 | 62464 | 62464.0 |
| 35AA | 17579 | 2585 | 1843 | 58 | 5516 | 5516.2 |

EXAMPLE 10

Comparison Of Aβ Peptide With/Without Addition Of Cysteine Between With And Without Addition Of Adjuvant (1) Preparation of Aβ Peptides with/without Addition of Cysteine

28AA:
(SEQ ID NO: 5)
DAEFRHDSGYEVHHQKLVFFAEDVGSNK

28AACys:
(SEQ ID NO: 6)
DAEFRHDSGYEVHHQKLVFFAEDVGSNKC

The above peptides were synthesized (Hokkaido System Science Co., Ltd.) and diluted with saline to obtain a 5 mg/mL stock solution. To 100 µL of the stock solution was added 900 µL of saline to 0.5 mg/mL of the concentration and the mixture was dispensed into 1.5 mL tube (immunogen) and stored at −80° C. or lower till use.

(2) Adjuvant

As an adjuvant, the commercially available Quil-A (Accurate Chemical & Scientific Corporation) and MPL+TDM emulsion (Corixa) were used. Quil-A was dissolved in saline to obtain 5 mg/mL of a stock solution. In addition, 1 vial of MPL+TDM emulsion was dissolved in 1 mL of saline to obtain a stock solution, which was stored at 4° C. till use.

(3) Immunized Mice

Male CS7BL/6 mice (9 weeks old, SPF) were purchased from Japan Charles River Co., Ltd. and bred in SPF environment.

(4) Immunization Groups

The 24 mice were divided into 6 groups each comprising 4 mice: Group 1 administered with 28AA; Group 2 administered with 28AA +Quil-A; Group 3 administered with 28AA+MPL+TDM emulsion; Group 4 administered with 2BAACys; Group 5 administered with 28AACys+Quil-A; and Group 6 administered with 28AACys+MPL+TDM emulsion.

(5) Dose And Preparation Of Sample For Administration

A dose of Aβ peptide was 100 μg per animal and 0.2mL of 500 μg/mL of sample for administration was administered. With respect to the group administered with 28AA and the group administered with 28AACys, 20 μL of each of the stock solution and 180 μL of saline were mixed and the mixture was stored at −80° C. until the administration. With respect to the group administered with 28AA +Quil-A and the group administered with 28AACys+Quil-A, 20 μL of each of the stock solution, 10 μL of 5 mg/mL the stock solution of Quil-A (50 μg per animal) and 170 μL of saline were mixed and the mixture was stored at −80° C. until the administration. With respect to the group administered with 28AA+MPL+TDM emulsion and the group administered with 28AACys+MPL+TDM emulsion, 90 μL of each of the stock solution and 660 μL of saline were mixed to prepared the stock solution for administration, which was stored at −80° C. 0.5 mL of the MPL+TDM emulsion stock solution was added just before administration to obtain suspension (for 4.5 individual).

(6) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 3 times at 2-week intervals.

(7) Blood Sampling

On Day 7 from the final 3rd immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(8) Measurement of Anti-Aβ IgG antibody

Measurement of the anti-Aβ IgG antibody was conducted as described above. Table 10 shows the calculated anti-Aβ antibody titer of the murine serum in each of the immunization Groups. As shown in Table 10, it was found that antibody induction against Aβ could hardly be observed for 28AA together with Quil-A but observed for 28AA together with MPL+TDM emulsion. In case of 28AACys, a high antibody titer could be observed either with Quil-A or with MPL+TDM emulsion. The antibody induction of 28AACys alone was similar to that of 28AA together with MPL+TDM emulsion.

Table 10

| | Antibody titer (ng/mL) | | | | |
| | Animal No. | | | | |
| Group | 1 | 2 | 3 | 4 | Mean |
| 1. 28AA | 37 | 72 | 37 | 27 | 43.2 |
| 2. 28AA + Quil-A | 84 | 52 | 283 | 78 | 124.2 |
| 3. 28AA + MPL + TDM Emulsion | 20602 | 25442 | 14814 | 8832 | 17422.6 |
| 4. 28AACys | 8847 | 9458 | 10446 | 48224 | 19243.7 |
| 5. 28AACys + Quil-A | 277061 | 809713 | 504433 | 55412 | 411654.9 |
| 6. 28AACys + MPL + TDM Emulsion | 455340 | 177449 | 111462 | 454037 | 299572.1 |

EXAMPLE 11

Pharmacological Evaluation Of Aβ Peptide With Addition Of Cysteine Using Alzheimer Disease Model Mice (1) Preparation of Aβ Peptide with Addition of Cysteine 35AACys:
(SEQ ID NO: 21)
DAEFRHDSGYEVHHQKLVFFAEDVGSNKGAIIGLMC The above peptide was synthesized (Hokkaido System Science Co., Ltd.) and diluted with saline to obtain a 5 mg/mL stock solution. To 100 μL of the stock solution was added 900 μL of saline to 0.5 mg/mL of the concentration and the mixture was dispensed into 1.5 mL tube (immunogen) and stored at −80° C. or lower till use.

(2) Immunized Mice

Transgenic mice (TG2576, female, 11 weeks old, SPF), which showed Alzheimer-like pathological condition with accumulation of human Aβ in the brain through expression of a human Aβ precursor protein, were purchased from Taconic Farms, Inc. and bred in SPF environment.

(3) Immunization Groups

The 6 mice were divided into 2 groups each comprising 3 mice: Group 1 administered with 35AACys; and Group 2 not administered (control).

(4) Immunization and Schedule

Each 200 μL/mouse of an immunogen was administered to mice using a 1 mL tuberculin syringe (Terumo, SS-01T2613S) intradermally or subcutaneously at the abdomen (dose per mouse: 100 μg). The mice were immunized 4 tunes at 2-week intervals from 18-week old and then at monthly intervals with a total of 11 immunizations.

(5) Blood Sampling

On Day 13 from the final immunization, blood was collected from the abdominal aorta of all mice under anesthesia with pentobarbital sodium (Kyoritsu Seiyaku Corporation, Somnopentyl). The sampling blood was transferred to the Microtainer (Becton Dickinson Co., Ltd), adequate clotting has occurred at room temperature and then centrifuged at 5,000 rpm for 10 min. Each of the separated serum was dispensed into two 0.5 mL tubes and stored at −80° C. or lower until measurement.

(6) Extraction of Human Aβ Deposited in Brain

After blood sampling, the cerebrum was isolated via craniotomy. A part of the frontal lobe was sectioned and weighed. Thereto was added TBS containing a proteinase inhibitor (Roche, Complete Protease Inhibitor Cocktail Set, 1 tablet/50 mL of solution) (20 mM Tris, 137 mM NaCl, pH7.6; hereinafter referred to as "CP/TBS") to 150 mg (wet weight of brain)/mL and the mixture was homogenized with a homogenizer made of Teflon (trademark). Then, the mixture was centrifuged at 12,000 g at 4° C. for 10 min. The supernatant was discarded and the resulting precipitate was resuspended in 1% TritonX-100/CP/TBS (in the same amount as that of CP/TBS above) and the suspension was vortexed for 1 min. The suspension was centrifuged at 12,000 g at 4° C. for 10 min. The supernatant was discarded and the resulting precipitate was resuspended in 2% SDS/CP/TBS (in the same amount as that of CP/TBS above) and the suspension was vortexed for 1 min. The suspension was further centrifuged at 12,000 g at 4° C. for 10 min. The resulting supernatant was used as a sample fraction containing the human Aβ deposited in the brain.

(7) Measurement of Anti-Aβ IgG antibody

Measurement of the anti-Aβ IgG antibody was conducted as described above.

(8) Measurement of Human Aβ Deposited in Brain

Measurement was performed using the human β amyloid (1-42) ELISA kit WAKO (WAKO, code number 296-64401). To a microtiter plate immobilized with a human antibody against Aβ (BAN50) was added a sample containing 50-fold diluted human Aβ at 100 μL/well. After overnight reaction at 4° C., each of the diluted samples added was discarded and the microtiter plate was washed 5 times with 350 μL/well of the wash solution in the kit. An HRP labeled antibody (BCO5) solution (100 μL) was added to each of the wells followed by 1 hour reaction at 4° C. After the reaction, the labeled antibody solution was discarded and the microtiter plate was washed 5 times with 350 μL/well of the wash solution. A TMB solution (chromogenic agent; 100 μL) was added to each of the wells, followed by 30 min. reaction at room temperature in the dark. Then, 100 μL/well of the stop solution was added to quench the enzymatic reaction and optical density at 450 nm was measured (OD450 value). A standard curve was made using the attached standard solution (human β amyloid (1-42), 20 pmoL/L). On the measurement of the samples, said standard solution was diluted with the standard dilution solution to 0.156, 0.3125, 0.625, 1.25, 2.5, 5, 10 pmol/mL. OD450 value of each of the diluted standard solution was measured simultaneously with the measurement of each of the sample. A human Aβ concentration in each of the samples was calculated using the resulting unit of the standards and the standard curve of OD450 value.

Tables 11 and 12 show the calculated anti-Aβ antibody titer in the murine serum and the concentration of human Aβ deposited in the brain of each of the immunization groups. As shown in Table 11, production of antibody against Aβ was observed for Alzheimer model mice immunized with 35AACys. Besides, as shown in Table 12, a concentration of human Aβ (hAβ) deposition in the brain was found to be lower than that with Alzheimer model mice with no administration. Thus, it was proved that Aβ peptide with addition of Cys was efficacious not only as a prophylactic (peptide vaccine) but also as a therapeutic agent.

Table 11

| Group | Antibody titer (ng/mL) | | | |
|---|---|---|---|---|
| | Animal No. | | | |
| | 1 | 2 | 3 | Mean |
| Group administered with 35AACys | 43085 | 159564 | 308485 | 170378.0 |
| Group not administered | 242 | 105 | 660 | 335.2 |

Table 12

| Group | hA β conc. (pmol/mL) | | | |
|---|---|---|---|---|
| | Animal No. | | | |
| | 1 | 2 | 3 | Mean |
| Group administered with 35AACys | 544 | 1137 | 2377 | 1353.0 |
| Group not administered | 4170 | 6379 | 4442 | 4997.1 |

Industrial Applicability

The immunogenic peptide that induces an enhanced immune response comprising an Aβ peptide or a portion thereof with addition or insertion of cysteine or with addition of a peptide containing cysteine and the gene fragment encoding said peptide of the present invention may be used as a safe and convenient means for immune stimulation in a peptide vaccine, a DNA vaccine and the like. Moreover, the Aβ peptide that induces an enhanced immune response or a portion thereof, prepared by a method for enhancing an immune response of the present invention, may be an efficacious medicament for preventing or treating of Alzheimer disease.

The invention claimed is:

1. A method for enhancing an immune response which comprises administering to a subject in need thereof an immunogenic peptide that induces an enhanced immune response consisting of amino acids selected from the group consisting of the 1st-29th, 1st-30th, 1st-31st, 1st-35th, 1st-36th, 1st-37th, 1st-38th, 1st-39th, 1st-41st and 1st-42nd of an amyloid β peptide with the insertion of cysteine-between the 18th and 19th amino acid residues, between the 25th and 26th amino acid residues, or between the 28th and 29th amino acid residues counted from the N-terminus of the amyloid β peptide.

2. The method of claim 1, further comprising administering an adjuvant with the immunogenic peptide.

3. The method of claim 1, wherein the immunogenic peptide has a cysteine inserted into the amyloid β peptide between the 18th and 19th amino acid residues counted from the N-terminus of the amyloid β peptide.

4. The method of claim 1, wherein the immunogenic peptide has a cysteine inserted into the amyloid β peptide between the 25th and 26th amino acid residues counted from the N-terminus of the amyloid β peptide.

5. The method of claim 1, wherein the immunogenic peptide has a cysteine inserted into the amyloid β peptide between the 28th and 29th amino acid residues counted from the N-terminus of the amyloid β peptide.

6. The method of claim 1, wherein the immunogenic peptide consists of an amino acid sequence selected from the group consisting of SEQ ID NO: 46, SEQ ID NO: 48, SEQ ID NO: 50, and SEQ ID NO: 52.

7. The method of claim 1, wherein the immunogenic peptide consists of the amino acid sequence of SEQ ID NO: 46.

8. The method of claim 1, wherein the immunogenic peptide consists of the amino acid sequence of SEQ ID NO: 48.

9. The method of claim 1, the immunogenic peptide consists of the amino acid sequence of SEQ ID NO: 50.

10. The method of claim 1, wherein the immunogenic peptide consists of the amino acid sequence of SEQ ID NO: 52.

11. A method for enhancing an immune response which comprises administering to a subject in need thereof as a DNA vaccine a vector containing a gene fragment encoding an amino acid sequence of an immunogenic peptide that induces an enhanced immune response consisting of amino acids selected from the group consisting of the 1st-29th, 1st-30th, 1st-31st, 1st-35th, 1st-36th, 1st-37th, 1st-38th, 1st-39th, 1st-41st and 1st-42nd of an amyloid β peptide with the insertion of cysteine-between the 18th and 19th amino acid residues, between the 25th and 26th amino acid residues, or between the 28th and 29th amino acid residues counted from the N-terminus of the amyloid β peptide.

12. The method of claim 11, wherein the immunogenic peptide has a cysteine inserted into the amyloid β peptide between the 18th and 19th amino acid residues counted from the N-terminus of the amyloid β peptide.

13. The method of claim 11, wherein the immunogenic peptide has a cysteine inserted into the amyloid β peptide between the 25th and 26th amino acid residues counted from the N-terminus of the amyloid β peptide.

14. The method of claim 11, wherein the immunogenic peptide has a cysteine inserted into the amyloid β peptide between the 28th and 29th amino acid residues counted from the N-terminus of the amyloid β peptide.

15. The method of claim 11, wherein the immunogenic peptide consists of an amino acid sequence selected from the group consisting of SEQ ID NO: 46, SEQ ID NO: 48, SEQ ID NO: 50, and SEQ ID NO: 52.

16. The method of claim 11, wherein the immunogenic peptide consists of the amino acid sequence of SEQ ID NO: 46.

17. The method of claim 11, wherein the immunogenic peptide consists of the amino acid sequence of SEQ ID NO: 48.

18. The method of claim 11, the immunogenic peptide consists of the amino acid sequence of SEQ ID NO: 50.

19. The method of claim 11, wherein the immunogenic peptide consists of the amino acid sequence of SEQ ID NO: 52.

* * * * *

SEQUENCE LISTING

<160> NUMBER OF SEQ ID NOS: 58

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Cys
            20                  25

<210> SEQ ID NO 2
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: DNA coding for amino acids sequence of
      synthesized peptide

<400> SEQUENCE: 2
gatgcagaat tccgacatga ctcaggatat gaagttcatc atcaaaaatt ggtgttcttt      60
gcagaagatg tgggttcatg t                                                81

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Cys
            20                  25

<210> SEQ ID NO 4
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA coding for amino acids sequence of
      synthesized peptide

<400> SEQUENCE: 4
gatgcagaat tccgacatga ctcaggatat gaagttcatc atcaaaaatt ggtgttcttt      60
gcagaagatg tgggttcaaa ctgt                                             84

<210> SEQ ID NO 5
<211> LENGTH: 28
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys
            20                  25
```

```
<210> SEQ ID NO 7
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA cording for amino acids sequense of
      synthesized peptide

<400> SEQUENCE: 7
gatgcagaat tccgacatga ctcaggatat gaagttcatc atcaaaaatt ggtgttcttt     60
gcagaagatg tgggttcaaa caaatgt                                        87

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Cys
            20                  25                  30

<210> SEQ ID NO 9
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA coding for amino acids sequence of
      synthesized peptide

<400> SEQUENCE: 9
gatgcagaat tccgacatga ctcaggatat gaagttcatc atcaaaaatt ggtgttcttt     60
gcagaagatg tgggttcaaa caaaggttgt                                     90

<210> SEQ ID NO 10
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Cys
            20                  25                  30

<210> SEQ ID NO 11
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: DNA coding for amino acids sequence of
     synthesized peptide

<400> SEQUENCE: 11
gatgcagaat tccgacatga ctcaggatat gaagttcatc atcaaaaatt ggtgttcttt      60
gcagaagatg tgggttcaaa caaaggtgca tgt                                   93

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 12

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Cys
            20                  25                  30

<210> SEQ ID NO 13
<211> LENGTH: 96
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: DNA coding for amino acids sequence of
     synthesized peptide

<400> SEQUENCE: 13
gatgcagaat tccgacatga ctcaggatat gaagttcatc atcaaaaatt ggtgttcttt      60
gcagaagatg tgggttcaaa caaaggtgca atctgt                                96

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 14

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Cys

<210> SEQ ID NO 15
<211> LENGTH: 99
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: DNA coding for amino acids sequence of
     synthesized peptide

<400> SEQUENCE: 15
gatgcagaat tccgacatga ctcaggatat gaagttcatc atcaaaaatt ggtgttcttt    60
gcagaagatg tgggttcaaa caaaggtgca atcatttgt                           99

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Cys

<210> SEQ ID NO 17
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 17
gatgcagaat tccgacatga ctcaggatat gaagttcatc atcaaaaatt ggtgttcttt    60
gcagaagatg tgggttcaaa caaaggtgca atcattggat gt                      102

<210> SEQ ID NO 18
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Cys
        35

<210> SEQ ID NO 19
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

```
<400> SEQUENCE: 19
gatgcagaat tccgacatga ctcaggatat gaagttcatc atcaaaaatt ggtgttcttt      60
gcagaagatg tgggttcaaa caaaggtgca atcattggac tctgt                    105

<210> SEQ ID NO 20
<211> LENGTH: 35
<212> TYPE: PRT
<213> ORGANISM: Homo sapiens

<400> SEQUENCE: 20

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met
        35

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Cys
        35

<210> SEQ ID NO 22
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 22
gatgcagaat tccgacatga ctcaggatat gaagttcatc atcaaaaatt ggtgttcttt      60
gcagaagatg tgggttcaaa caaaggtgca atcattggac tcatgtgt                 108

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 23

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Cys
        35

<210> SEQ ID NO 24
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 24
gatgcagaat tccgacatga ctcaggatat gaagttcatc atcaaaaatt ggtgttcttt      60
gcagaagatg tgggttcaaa caaaggtgca atcattggac tcatggtgtg t              111

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Cys
        35

<210> SEQ ID NO 26
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 26
gatgcagaat tccgacatga ctcaggatat gaagttcatc atcaaaaatt ggtgttcttt      60
gcagaagatg tgggttcaaa caaaggtgca atcattggac tcatggtggg ctgt           114

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 27

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Cys
        35

<210> SEQ ID NO 28
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 28
gatgcagaat tccgacatga ctcaggatat gaagttcatc atcaaaaatt ggtgttcttt      60
gcagaagatg tgggttcaaa caaaggtgca atcattggac tcatggtggg cggttgt       117

<210> SEQ ID NO 29
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Cys
        35                  40

<210> SEQ ID NO 30
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 30
gatgcagaat tccgacatga ctcaggatat gaagttcatc atcaaaaatt ggtgttcttt      60
gcagaagatg tgggttcaaa caaaggtgca atcattggac tcatggtggg cggtgtttgt    120

<210> SEQ ID NO 31
<211> LENGTH: 40
<212> TYPE: PRT
<213> ORGANISM: Homo sapiens
```

<400> SEQUENCE: 31

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 32
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Cys
        35                  40

<210> SEQ ID NO 33
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 33
gatgcagaat tccgacatga ctcaggatat gaagttcatc atcaaaaatt ggtgttcttt      60
gcagaagatg tgggttcaaa caaaggtgca atcattggac tcatggtggg cggtgttgtc    120
tgt                                                                   123

<210> SEQ ID NO 34
<211> LENGTH: 42
<212> TYPE: PRT
<213> ORGANISM: Homo sapiens

<400> SEQUENCE: 34

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 35
<211> LENGTH: 126
<212> TYPE: DNA
<213> ORGANISM: Homo sapiens

```
<400> SEQUENCE: 35
gatgcagaat tccgacatga ctcaggatat gaagttcatc atcaaaaatt ggtgttcttt    60
gcagaagatg tgggttcaaa caaaggtgca atcattggac tcatggtggg cggtgttgtc   120
atagcg                                                              126

<210> SEQ ID NO 36
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Cys
        35                  40

<210> SEQ ID NO 37
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 37
gatgcagaat tccgacatga ctcaggatat gaagttcatc atcaaaaatt ggtgttcttt    60
gcagaagatg tgggttcaaa caaaggtgca atcattggac tcatggtggg cggtgttgtc   120
atagcgtgt                                                           129

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys Cys
            20                  25                  30

<210> SEQ ID NO 39
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA coding for amino acids sequence of
      synthesized peptide
```

<400> SEQUENCE: 39
gatgcagaat tccgacatga ctcaggatat gaagttcatc atcaaaaatt ggtgttcttt    60
gcagaagatg tgggttcaaa caaatgttgt                                    90

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Asp Ala Glu Phe Arg His Asp Ser Gly Tyr Glu Val His His Gln
1               5                   10                  15

Lys Leu Val Phe Phe Ala Glu Asp Val Gly Ser Asn Lys
            20                  25

<210> SEQ ID NO 41
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA coding for amino acids sequence of
      synthesized peptide

<400> SEQUENCE: 41
tgtgatgcag aattccgaca tgactcagga tatgaagttc atcatcaaaa attggtgttc    60
tttgcagaag atgtgggttc aaacaaa                                       87

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Cys Asp Ala Glu Phe Arg His Asp Ser Gly Tyr Glu Val His His Gln
1               5                   10                  15

Lys Leu Val Phe Phe Ala Glu Asp Val Gly Ser Asn Lys Cys
            20                  25                  30

<210> SEQ ID NO 43
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA coding for amino acids sequence of
      synthesized peptide

<400> SEQUENCE: 43
tgtgatgcag aattccgaca tgactcagga tatgaagttc atcatcaaaa attggtgttc    60
tttgcagaag atgtgggttc aaacaaatgt                                    90

```
<210> SEQ ID NO 44
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ala Glu Phe Arg His Asp Cys Ser Gly Tyr Glu Val His His Gln
1               5                   10                  15

Lys Leu Val Phe Phe Ala Glu Asp Val Gly Ser Asn Lys
            20                  25

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Ala Glu Phe Arg His Asp Ser Gly Tyr Cys Glu Val His His Gln
1               5                   10                  15

Lys Leu Val Phe Phe Ala Glu Asp Val Gly Ser Asn Lys
            20                  25

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ala Glu Phe Arg His Asp Ser Gly Tyr Glu Val His His Gln Lys
1               5                   10                  15

Leu Val Cys Phe Phe Ala Glu Asp Val Gly Ser Asn Lys
            20                  25

<210> SEQ ID NO 47
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA coding for amino acids sequence of
      synthesized peptide

<400> SEQUENCE: 47
gatgcagaat tccgacatga ctcaggatat gaagttcatc atcaaaaatt ggtgtgtttc    60
tttgcagaag atgtgggttc aaacaaa                                       87

<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 48

Asp Ala Glu Phe Arg His Asp Ser Gly Tyr Glu Val His His Gln Lys
1               5                   10                  15

Leu Val Phe Phe Ala Glu Asp Val Gly Cys Ser Asn Lys
            20                  25

<210> SEQ ID NO 49
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA coding for amino acids sequence of
      synthesized peptide

<400> SEQUENCE: 49
gatgcagaat tccgacatga ctcaggatat gaagttcatc atcaaaaatt ggtgttcttt      60
gcagaagatg tgggttgttc aaacaaa                                         87

<210> SEQ ID NO 50
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys Gly Ala Ile
            20                  25                  30

Ile Gly

<210> SEQ ID NO 51
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 51
gatgcagaat tccgacatga ctcaggatat gaagttcatc atcaaaaatt ggtgttcttt      60
gcagaagatg tgggttcaaa caaatgtggt gcaatcattg ga                        102

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys Gly Ala Ile
            20                  25                  30

Ile Gly Leu Met
        35

<210> SEQ ID NO 53
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 53
gatgcagaat tccgacatga ctcaggatat gaagttcatc atcaaaaatt ggtgttcttt      60
gcagaagatg tgggttcaaa caaatgtggt gcaatcattg gactcatg                 108

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys Thr Thr Asp
            20                  25                  30

<210> SEQ ID NO 55
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA coding for amino acids sequence of
      synthesized peptide

<400> SEQUENCE: 55
gatgcagaat tccgacatga ctcaggatat gaagttcatc atcaaaaatt ggtgttcttt      60
gcagaagatg tgggttcaaa caaatgtact actgac                              96

<210> SEQ ID NO 56
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 56

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys Glu Ile Phe
            20                  25                  30

Glu Phe Thr Thr Asp
        35

<210> SEQ ID NO 57
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA coding for amino acids sequence of
      synthesized peptide

<400> SEQUENCE: 57
gatgcagaat tccgacatga ctcaggatat gaagttcatc atcaaaaatt ggtgttcttt      60
gcagaagatg tgggttcaaa caaatgtgaa atcttcgaat tcactactga c              111

<210> SEQ ID NO 58
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys
            20                  25
```